US011613755B2

(12) United States Patent
Cheng et al.

(10) Patent No.: US 11,613,755 B2
(45) Date of Patent: Mar. 28, 2023

(54) NUCLEIC ACID-DRUG COMPLEX AND USE THEREOF

(71) Applicant: Industrial Technology Research Institute, Hsinchu (TW)

(72) Inventors: Ping-Fu Cheng, Taipei (TW); Ya-Ling Chiu, Hsinchu (TW); Kang-Li Wang, Kaohsiung (TW); Po-Yen Lin, Hsinchu (TW); Shih-Ta Chen, New Taipei (TW); Tseng-Huang Liu, Kaohsiung (TW); Pei-Shin Jiang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 17/132,793

(22) Filed: Dec. 23, 2020

(65) Prior Publication Data
US 2021/0230600 A1    Jul. 29, 2021

Related U.S. Application Data

(60) Provisional application No. 62/955,690, filed on Dec. 31, 2019.

(51) Int. Cl.
| | |
|---|---|
| *C12N 15/115* | (2010.01) |
| *A61K 47/54* | (2017.01) |
| *A61P 35/00* | (2006.01) |
| *A61K 9/00* | (2006.01) |
| *C12N 15/113* | (2010.01) |

(52) U.S. Cl.
CPC .......... *C12N 15/115* (2013.01); *A61K 9/0019* (2013.01); *A61K 47/549* (2017.08); *A61P 35/00* (2018.01); *C12N 15/1138* (2013.01); *C12N 2310/16* (2013.01); *C12N 2310/31* (2013.01); *C12N 2310/315* (2013.01); *C12N 2310/3519* (2013.01); *C12N 2320/32* (2013.01)

(58) Field of Classification Search
CPC .............. C12N 15/115; C12N 15/1138; C12N 2310/16; C12N 2310/31; C12N 2310/315; C12N 2310/3519; C12N 2320/32; A61K 9/0019; A61K 47/549; A61P 35/00
See application file for complete search history.

(56) References Cited

U.S. PATENT DOCUMENTS

| | | | |
|---|---|---|---|
| 7,745,606 B2 | 6/2010 | Dina et al. | |
| 10,100,316 B2 | 10/2018 | Epstein et al. | |
| 2004/0253679 A1* | 12/2004 | Epstein ................ | C12N 15/115 |
| | | | 435/325 |
| 2005/0124565 A1 | 6/2005 | Diener et al. | |
| 2016/0346312 A1* | 12/2016 | Guiducci ............. | A61K 31/713 |
| 2017/0290923 A1 | 10/2017 | Li et al. | |
| 2018/0258431 A1 | 9/2018 | Yang et al. | |
| 2018/0369411 A1 | 12/2018 | Yu et al. | |
| 2019/0136240 A1 | 5/2019 | Weiner et al. | |
| 2019/0233824 A1 | 8/2019 | Thangavelu Devaraj et al. | |

FOREIGN PATENT DOCUMENTS

| | | |
|---|---|---|
| JP | 2007-525177 A | 9/2007 |
| JP | 2018-502120 A | 1/2018 |
| WO | WO 2004/094614 A2 | 11/2004 |
| WO | WO 2016/109310 A1 | 7/2016 |
| WO | WO 2016/196173 A1 | 12/2016 |
| WO | WO 2017/040620 A1 | 3/2017 |
| WO | WO 2018/095697 A1 | 5/2018 |
| WO | WO 2018/119313 A1 | 6/2018 |
| WO | WO 2019/168467 A1 | 9/2019 |

OTHER PUBLICATIONS

Extended European Search Report far European Application No. 20217127.8, dated May 21, 2021.
Han et al., "Immune lipoprotein nanostructures inspired relay drug delivery for amplifying antitumor efficiency," Biomaterials, vol. 185, XP55802581, Sep. 2018, pp. 205-218 (14 pages total).
Hanagata, "CpG oligodeoxynucleolide nanomedicines for the prophylaxis or treatment of cancers, infectious diseases, and allergies," International Journal of Nanomedicine, vol. 12, XP055551376, Jan. 2017, pp. 515-531 (18 pages total).
Prodeus et al., "Targeting the PD-1/PD-L1 Immune Evasion Axis With DNA Aptamers as a Novel Therapeutic Strategy for the Treatment of Disseminated Cancers" Molecular Therapy—Nucleic Acids. vol. 4, No. 4, XP055310846, Apr. 2015, pp. 1-10.
Taiwanese Office Action and Search Report for Taiwanese Application No. 109145837, dated Dec. 20, 2021.
Wei et al., "One-Step Self-Assembly of Multifunctional DNA Nanohydrogels: An Enhanced and Harmless Strategy for Guiding Combined Antitumor Therapy," Applied Materials and Interfaces, vol. 11, No. 50, XP55802535, Nov. 2019, pp. 46479-46489 (12 pages total).
Wu et al., "Selection of Oligonucleotide Aptamers with Enhanced Uptake and Activation of Human Leukemia B Cells" Human Gene Therapy, vol. 14, No. 9, XP55802564, Jun. 2003, pp. 849-860 (14 pages total).
Japanese Office Action for corresponding Japanese Application No. 2020-214352, dated Mar. 31, 2022.

\* cited by examiner

*Primary Examiner* — J. E. Angell

(74) *Attorney, Agent, or Firm* — Birch, Stewart, Kolasch & Birch, LLP

(57) ABSTRACT

A nucleic acid-drug complex is provided in the present disclosure, which includes a nucleic acid sequence of an anti-PD-L1 aptamer and a CpG oligonucleotide sequence capable of activating TLR9, in which the CpG oligonucleotide sequence consists of a first fragment and a second fragment, and the nucleic acid sequence of the anti-PD-L1 aptamer is inserted between the first fragment and the second fragment.

13 Claims, 9 Drawing Sheets

Specification includes a Sequence Listing.

NUCLEIC ACID-DRUG COMPLEX AND USE THEREOF

CROSS REFERENCE TO RELATED APPLICATIONS

This application claims the benefit of U.S. Provisional Application No. 62/955,690, filed Dec. 31, 2019, the entirety of which is incorporated by reference herein.

A sequence listing submitted as a text file via EFS-Web is incorporated herein by reference. The text file containing the sequence listing is named "9044B-A27203-US_Seq_Listing_F.txt"; its date of creation was Mar. 16, 2021; and its size is 9.73 kilobytes.

BACKGROUND

Technical Field

The present disclosure relates to a nucleic acid-drug complex, and in particular it relates to a nucleic acid-drug complex of anti-PD-L1 aptamer and use thereof.

Description of the Related Art

Programmed death-1 (PD-1) is a co-stimulator of activated T cell expression and performs negative regulation in the immune system, which can inhibit the activation and proliferation of T cells. PD-L1, the ligand of PD-1, has immunosuppressive properties and is expressed on some antigen-expressing cells of vascular endothelial system of non-lymphoid tissues, such as dendritic cells (DC), macrophages and B cells. Moreover, since PD-L1 is also expressed on many tumor cells, stromal cells and immune cells, blocking the binding of PD-1 and PD-L1 can effectively enhance the immune response and have an anti-tumor effect. Checkpoint blockade immunotherapy modulated by anti-PD-1 and anti-PD-L1 antibodies has been used in clinical treatment.

On the other hand, CpG oligodeoxynucleotides (CpG ODNs) are a series of deoxynucleotides having a strong immune activation effect, which can effectively activate a variety of immune cells, trigger an immune response, and provide a significant anti-cancer effect. However, intratumoral injection (IT) is currently a safe and effective way of administering CpG oligodeoxynucleotides, and this situation limits the applicable indications of CpG oligodeoxynucleotides.

The combination of multiple drugs is often used in current immunotherapy, for example, the combined use of anti-PD-L1 antibodies and CpG oligodeoxynucleotides. However, the combined use of drugs may cause many potential risks and may also burden patients. Therefore, the development of the immunotherapy that has effective anti-cancer effects and can be administered alone is still one of the research goals in the pharmaceutical industry.

SUMMARY

In accordance with some embodiments of the present disclosure, a nucleic acid-drug complex is provided, which includes a nucleic acid sequence of an anti-PD-L1 aptamer and a CpG oligonucleotide sequence capable of activating TLR9. The anti-PD-L1 aptamer binds to PD-L1. The CpG oligonucleotide sequence binds to TLR9 receptor. The CpG oligonucleotide sequence consists of a first fragment and a second fragment, and the nucleic acid sequence of the anti-PD-L1 aptamer is inserted between the first fragment and the second fragment.

In accordance with some embodiments of the present disclosure, a use of the aforementioned nucleic acid-drug complex is provided, which is used to manufacture a drug for treatment of cancer.

In accordance with some embodiments of the present disclosure, a pharmaceutical composition is provided. The pharmaceutical composition includes the aforementioned nucleic acid-drug complex and a pharmaceutically acceptable carrier.

A detailed description is given in the following embodiments with reference to the accompanying drawings.

DETAILED DESCRIPTION

Figure 1A:
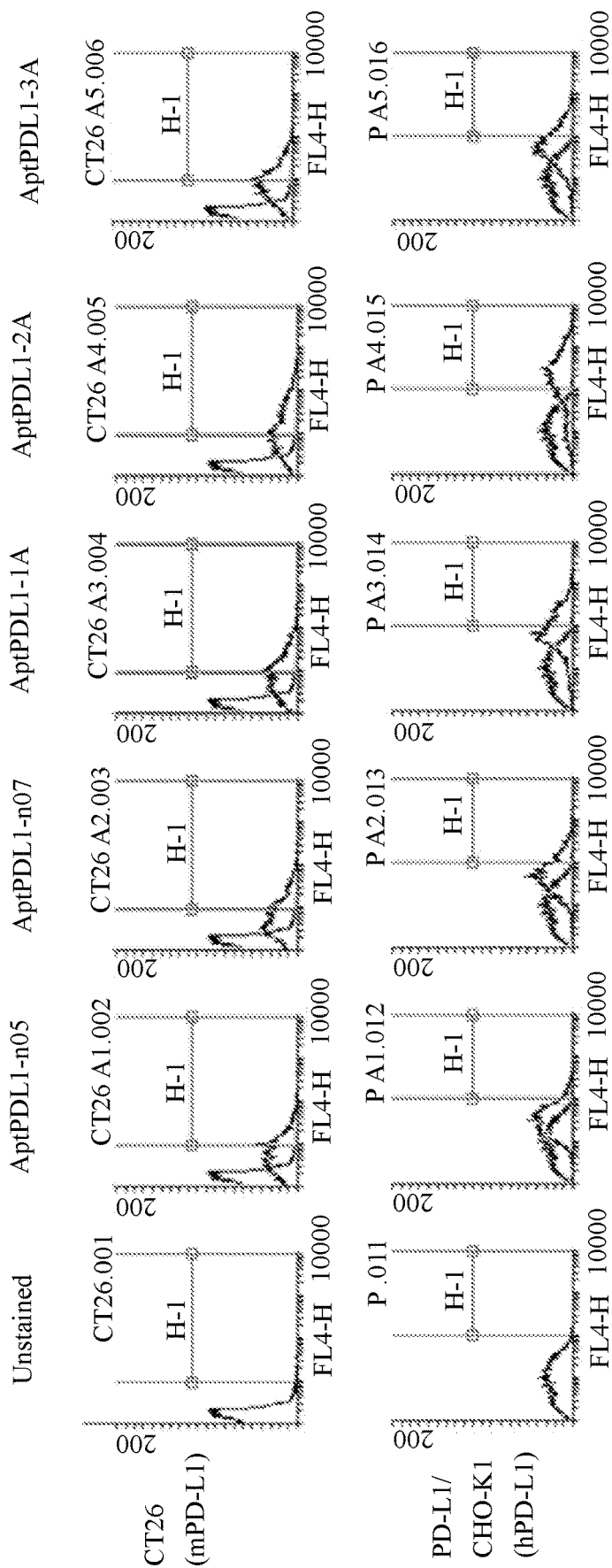
FIG. 1A shows the analysis result of binding affinity for PD-L1 of samples, "Unstained" (negative control group), "AptPDL1-n05", "AptPDL1-n07", "AptPDL1-1A", "AptPDL1-2A", and "AptPDL1-3A", using a flow cytometer in accordance with some embodiments of the present disclosure.

The nucleic acid-drug complex of the present disclosure is described in detail in the following description. It should be understood that in the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent that the exemplary embodiments set forth herein are used merely for the purpose of illustration and not the limitation of the present disclosure.

Unless defined otherwise, all technical and scientific terms used herein have the same meaning as commonly understood by one of ordinary skill in the art to which this disclosure belongs. It should be appreciated that, in each case, the term, which is defined in a commonly used dictionary, should be interpreted as having a meaning that conforms to the relative skills of the present disclosure and the background or the context of the present disclosure, and should not be interpreted in an idealized or overly formal manner unless so defined.

The terms "oligonucleotide", "polynucleotide", "nucleic acid" and "nucleic acid molecule" may be used interchangeably herein and refer to the polymer of nucleotides of any length, which may include a single-stranded DNA (ssDNA), double-stranded DNA (dsDNA), single-stranded RNA (ssRNA) and double-stranded RNA (dsRNA). Nucleotides may be deoxyribonucleotides, ribonucleotides, or modified nucleotides. Nucleosides may consist of purine (adenine (A) or guanine (G) or its derivatives) or pyrimidine (thymine (T), cytosine (C) or uracil (U) or its derivatives) bases and sugar bonds. The four nucleoside units (or bases) in DNA are called deoxyadenosine, deoxyguanosine, deoxythymidine and deoxycytidine. The four nucleoside units (or bases) in RNA are called adenosine, guanosine, uridine and cytidine. Nucleotides are phosphate esters of nucleosides.

The terms "CpG" and "CG" may be used interchangeably herein and refer to cytosine and guanine separated by a phosphodiester bond. In accordance with the embodiments of the present disclosure, the oligonucleotide may include one or more unmethylated CpG dinucleotides. In accordance with some embodiments of the present disclosure, the oligonucleotide may be an oligodeoxynucleotide (ODN).

The term "programmed death ligand-1", also known as "PD-L1", "cluster of differentiation 274 (CD274)" or "B7 homolog-1 (B7-H1)", refers to the protein encoded by CD274 gene in humans. Human PD-L1 is a 40 kDa type 1 transmembrane protein, whose main function is suppressing the immune system. PD-L1 binds to the receptor PD-1 on activated T cells, B cells and bone marrow cells to regulate activation or inhibition. PD-L1 also has a significant affinity for the costimulatory molecule CD80 (B7-1). The binding of PD-L1 to the receptor PD-1 on T cells can transmit a signal that can inhibit the production of IL-2 regulated by the T cell receptor and the activation of T cell proliferation. PD-L1 can be regarded as a checkpoint, and its increase in tumors facilitates the inhibition of the anti-tumor response regulated by T cells. In accordance with some embodiments of the present disclosure, PD-L1 may be PD-L1 derived from mammals, for example, may be PD-L1 derived from humans.

The term "cancer" refers to a physiological condition characterized by unregulated cell growth in a cell population in a mammal. The term "tumor" refers to any tissue mass produced by excessive cell growth or proliferation, which includes benign (non-cancerous) or malignant (cancerous) tumors, including precancerous lesions.

The term "immune response" includes the response from the innate immune system and the acquired immune system, which includes a cell-regulated immune response or a humoral immune response. The immune response includes T cell and B cell responses, as well as responses from other cells of the immune system, such as natural killer (NK) cells, monocytes, macrophages, etc.

Furthermore, the term "treatment" refers to a therapeutic measure that cures or alleviates the diagnosed pathological symptom or disease, reduces and/or stops the progression of the disease, and the preventive measures to prevent and/or alleviate the development of the target pathological symptom or disease. Therefore, the individuals in need of treatment may include those who already have a disease, those who are susceptible to a disease, and those who are to be prevented a disease. In accordance with the embodiments of the present disclosure, if a patient with cancer or tumor shows one or more conditions as follow, it means that the individual has been successfully treated: increased immune response, increased anti-tumor response, increased cytolytic activity of immune cells, and increased killing tumor cells by immune cells, decreased cancer cells or not existed at all; decreased tumor size; inhibited or absent cancer cell infiltration into surrounding organs; inhibited or absent tumor or cancer cell metastasis; inhibited or absent cancer cell growth; remission of one or more symptoms associated with a specific cancer; reduced morbidity and mortality; improved life quality; reduced tumorigenicity; or decreased number or occurrence frequency of cancer stem cells, etc.

In accordance with some embodiments of the present disclosure, a nucleic acid-drug complex is provided, which includes a nucleic acid sequence of an anti-PD-L1 aptamer that binds to PD-L1 and a CpG oligonucleotide sequence that binds to a TLR9 (Toll-like receptor 9) receptor. In addition, the nucleic acid sequence of the anti-PD-L1 aptamer is inserted between a first fragment and a second fragment of the CpG oligonucleotide sequence. The novel nucleic acid-drug complex provided in the embodiments of the present disclosure combines the CpG oligonucleotide sequence that can activate TLR9 and the anti-PD-L1 aptamer. The nucleic acid-drug complex has tumor targetability and multiple immunomodulatory activities, can be administered systemically by intravenous injection, and can be administered alone, which can replace multi-drug combination immunotherapy.

In accordance with some embodiments, the nucleic acid sequence of the anti-PD-L1 aptamer has at least 85%, for example, 86%, 87%, 88%, 89%, 90%, 91%, 92%, 93%, 94%, 95%, 96%, 97%, 98% or 99% similarity to the sequence shown in any one of SEQ ID NOs: 1 to 9, but it is not limited thereto. In accordance with some embodiments, the anti-PD-L1 aptamer consists of the nucleic acid sequence shown in any one of SEQ ID NOs: 1 to 9. In accordance with some embodiments, the nucleotides in the nucleic acid sequence of the anti-PD-L1 aptamer will be paired to form a specific secondary structure, and the anti-PD-L1 aptamer can bind to PD-L1 through such a secondary structure and block the binding site of PD-1 and PD-L1, thereby maintaining or strengthening the anti-tumor immune response.

In accordance with some embodiments, the nucleic acid-drug complex includes the aforementioned nucleic acid sequence of the anti-PD-L1 aptamer and the CpG oligonucleotide sequence. The CpG oligonucleotide sequence can bind to the TLR9 receptor, and the CpG oligonucleotide sequence can strongly activate TLR9, promote the production of interferon, and induce immune responses such as anti-tumor or anti-virus responses. In accordance with some embodiments, the CpG oligonucleotide is an oligodeoxynucleotide (ODN). In accordance with some embodiments, the CpG oligonucleotide sequence may have at least 85%, for example, 86%, 87%, 88%, 89%, 90%, 91%, 92%, 93%, 94%, 95%, 96%, 97%, 98% or 99% similarity to the nucleic acid sequence shown in any one of SEQ ID NOs: 10 to 23, but it is not limited thereto. In accordance with some embodiments, the CpG oligonucleotide sequence may consist of a first fragment and a second fragment. In accordance with some embodiments, the first fragment and the second fragment of the CpG oligonucleotide sequence may be selected from the nucleic acid sequence shown in any one of SEQ ID NOs:10 to 23.

In other words, in accordance with some embodiments, the sequence consists of the first fragment and the second fragment of the CpG oligonucleotide sequence may have at least 85%, for example, 86%, 87%, 88%, 89%, 90%, 91%, 92%, 93%, 94%, 95%, 96%, 97%, 98% or 99% similarity to the nucleic acid sequence shown in any one of SEQ ID NOs: 10 to 23, but it is not limited thereto. In accordance with some embodiments, the first fragment and the second fragment of the CpG oligonucleotide sequence together constitute the nucleic acid sequence shown in any one of SEQ ID NOs:10 to 23, that is, the CpG oligonucleotide sequence is a nucleic acid sequence shown in any one of SEQ ID NOs:10 to 23.

It should be noted that, in accordance with the embodiments of the present disclosure, the nucleic acid sequence of the anti-PD-L1 aptamer is inserted between the first fragment and the second fragment of the CpG oligonucleotide sequence, so that the nucleic acid-drug complex can have both tumor targetability and multiple immunomodulatory activities. In accordance with some embodiments, the nucleic acid sequence of the anti-PD-L1 aptamer and the CpG oligonucleotide sequence may be connected through a linker. In accordance with some embodiments, the nucleic acid sequence of the anti-PD-L1 aptamer and the CpG oligonucleotide sequence may also be connected without additional designed linkers.

In accordance with some embodiments, the ratio of the length of the first fragment of the CpG oligonucleotide sequence to the length of the second fragment of the CpG oligonucleotide sequence is about 1:15 to 15:1, or about 1:10 to 10:1. For example, the ratio of the length of the first fragment of the CpG oligonucleotide sequence to the length of the second fragment of the CpG oligonucleotide sequence may be about 1:1, 1:2, 1:3, 1:4, 1:5, 1:6, 1:7, 1:8, 1:9, 9:1, 8:1, 7:1, 6:1, 5:1, 4:1, 3:1 or 2:1, but it is not limited thereto. In accordance with some embodiments, the length of the CpG oligonucleotide sequence (i.e. the total length of the sum of the length of the first fragment and the length of the second fragment) may be in a range from about 15 to 40 nucleotides, or about 20 to 35 nucleotides, or about 20 to 30 nucleotides, for example, about 21, 22, 23, 24, 25, 26, 27, 28 or 29 nucleotides, but it is not limited thereto.

Furthermore, in accordance with some embodiments, the CpG oligonucleotide sequence may include one or more unmethylated CpG motifs. In accordance with some embodiments, 85% to 100% of the CpG motif in the CpG oligonucleotide sequence may be unmethylated, for example, about 88%, 90%, 92%, 95%, 98%, etc. of the CpG motif may be unmethylated, but it is not limited thereto. In accordance with some embodiments, all CpG motifs in the CpG oligonucleotide sequence may be unmethylated. In addition, in accordance with some embodiments, the CpG oligonucleotide sequence may include a modified phosphodiester bond, such as a phosphorothioate bond, thereby reducing the risk of the nucleic acid-drug complex being degraded by enzymes in the organism, and improving the stability of the nucleic acid-drug complex. In accordance with some embodiments, 70% to 100%, or about 80% to 100%, for example, 85%, 90% or 95%, of phosphodiester bonds in the CpG oligonucleotide sequence are phosphorothioate bonds, but it is not limited thereto. In accordance with some embodiments, all phosphodiester bonds in the CpG oligonucleotide sequence may be modified to phosphorothioate bonds. In accordance with some embodiments, all phosphodiester bonds in the CpG oligonucleotide sequence can be modified to phosphorothioate bonds.

In accordance with some embodiments, the nucleic acid sequence of the nucleic acid-drug complex may have at least 85%, for example, 86%, 87%, 88%, 89%, 90%, 91%, 92%, 93%, 94%, 95%, 96%, 97%, 98% or 99% similarity to the nucleic acid sequence shown in any one of SEQ ID NOs: 29 to 34, but it is not limited thereto. In accordance with some embodiments, the nucleic acid-drug complex consists of the nucleic acid sequence shown in any one of SEQ ID NOs: 29 to 34.

Specifically, the nucleic acid sequence of SEQ ID NO: 29 is a combination of the anti-PD-L1 aptamer of SEQ ID NO: 1 and the CpG oligonucleotide sequence of SEQ ID NO: 10, and the nucleic acid sequence of SEQ ID NO: 1 can be inserted into the nucleic acid sequence of SEQ ID NO: 10, and SEQ ID NO: 10 is divided into the first fragment with 15 nucleotides and the second fragment with 15 nucleotides. In addition, all phosphodiester bonds in the CpG oligonucleotide sequence of SEQ ID NO: 10 can be modified to phosphorothioate bonds.

The nucleic acid sequence of SEQ ID NO: 30 is a combination of the anti-PD-L1 aptamer of SEQ ID NO: 2 and the sequence having 96% similarity to the CpG oligonucleotide sequence of SEQ ID NO: 10 (two Ts were added at 5' end, and the second A at 3' end is replaced with T), and the nucleic acid sequence of SEQ ID NO: 2 can be inserted into the sequence having 96% similarity to the CpG oligonucleotide sequence of SEQ ID NO: 10, and this sequence is divided into the first fragment with 17 nucleotides and the second fragment with 15 nucleotides. In addition, only the two phosphodiester bonds respectively located at the 5' and 3' ends in this sequence are modified to phosphorothioate bonds.

The nucleic acid sequence of SEQ ID NO: 31 is a combination of the anti-PD-L1 aptamer of SEQ ID NO: 3 and the CpG oligonucleotide sequence of SEQ ID NO: 10, and the nucleic acid sequence of SEQ ID NO: 3 can be inserted into the nucleic acid sequence of SEQ ID NO: 10, and SEQ ID NO: 10 is divided into the first fragment with 15 nucleotides and the second fragment with 15 nucleotides. In addition, all phosphodiester bonds in the CpG oligonucleotide sequence of SEQ ID NO: 10 can be modified to phosphorothioate bonds.

The nucleic acid sequence of SEQ ID NO: 32 is a combination of the anti-PD-L1 aptamer of SEQ ID NO: 3 and the CpG oligonucleotide sequence of SEQ ID NO: 22, and the nucleic acid sequence of SEQ ID NO: 3 can be inserted into the nucleic acid sequence of SEQ ID NO: 22, and SEQ ID NO: 22 is divided into the first fragment with 15 nucleotides and the second fragment with 15 nucleotides. In addition, all phosphodiester bonds in the CpG oligonucleotide sequence of SEQ ID NO: 22 can be modified to phosphorothioate bonds.

The nucleic acid sequence of SEQ ID NO: 33 is a combination of the anti-PD-L1 aptamer of SEQ ID NO: 3 and the CpG oligonucleotide sequence of SEQ ID NO: 23, and the nucleic acid sequence of SEQ ID NO: 3 can be inserted into the nucleic acid sequence of SEQ ID NO: 23, and SEQ ID NO: 23 is divided into the first fragment with 15 nucleotides and the second fragment with 15 nucleotides. In addition, all phosphodiester bonds in the CpG oligonucleotide sequence of SEQ ID NO: 23 can be modified to phosphorothioate bonds.

The nucleic acid sequence of SEQ ID NO: 34 is a combination of the anti-PD-L1 aptamer of SEQ ID NO: 7 and the CpG oligonucleotide sequence of SEQ ID NO: 10, and the nucleic acid sequence of SEQ ID NO: 7 can be inserted into the nucleic acid sequence of SEQ ID NO: 10, and SEQ ID NO: 10 is divided into the first fragment with 15 nucleotides and the second fragment with 15 nucleotides. In addition, all phosphodiester bonds in the CpG oligonucleotide sequence of SEQ ID NO: 10 can be modified to phosphorothioate bonds.

Furthermore, in accordance with some embodiments, the aforementioned nucleic acid-drug complex can be used to manufacture a drug for treating cancer. In addition, in accordance with some embodiments, a pharmaceutical composition is provided, which includes the aforementioned nucleic acid-drug complex and a pharmaceutically acceptable carrier. The pharmaceutical composition can be used for treatment of cancer. For example, in accordance with some embodiments, an effective amount of the pharmaceutical composition including the aforementioned nucleic acid-drug complex can be administered to an individual in need. In accordance with some embodiments, the individual may include a mammal, such as mouse, rat, guinea pig, rabbit, dog, cat, monkey, orangutan, or human, etc., but it is not limited thereto. In accordance with some embodiments, the individual may be a human. In accordance with some embodiments, the pharmaceutical composition can be administered by intravenous injection, intratumoral injection, and subcutaneous injection, but it is not limited thereto. In accordance with some embodiments, the pharmaceutical composition may be administered by intravenous injection.

In accordance with some embodiments, the aforementioned cancers may include colon cancer, breast cancer, lung cancer, pancreatic cancer, liver cancer, stomach cancer, esophageal cancer, head and neck squamous cell carcinoma, prostate cancer, bladder cancer, lymphoma, gallbladder cancer, kidney cancer, blood cancer, colorectal cancer, multiple myeloma, ovarian cancer, cervical cancer or glioma, but it is not limited thereto.

In accordance with some embodiments, the pharmaceutical composition may present in the form of a solution or suspension. Alternatively, the pharmaceutical composition may be a dehydrated solid (e.g., a lyophilized or spray-dried solid). In accordance with some embodiments, the pharmaceutical composition may be sterile and non-toxic to the individual. Moreover, in accordance with some embodiments, the aforementioned pharmaceutically acceptable carrier may include excipients, solubilizers, buffers, stabilizers or preservatives, but it is not limited thereto.

For example, the excipient may include a solvent. In accordance with some embodiments, the pharmaceutical composition may include an aqueous vehicle as a solvent. The aqueous vehicle may include, for example, sterile water, saline solution, phosphate buffered saline, or Ringer's solution, but it is not limited thereto. In accordance with some embodiments, the solubilizer is a protective agent that helps stabilize the nucleic acid-drug complex and prevent its degradation during lyophilization or spray-drying and/or during storage. The solubilizer may include, for example, sugars (monosaccharides, disaccharides, and polysaccharides), such as sucrose, lactose, trehalose, mannitol, sorbitol, or glucose, but it is not limited thereto. Furthermore, in accordance with some embodiments, the buffer can control the pH value to prevent degradation of the nucleic acid-drug complex during processing, storage, and the like. For example, the buffer may include salts such as acetate, citrate, phosphate, or sulfate, but it is not limited thereto. For example, the buffer may also include amino acids, such as arginine, glycine, histidine or lysine, but it is not limited thereto. In accordance with some embodiments, the stabilizer may include, for example, dextrose, glycerol, sodium chloride, glycerol, or mannitol, but it is not limited thereto. In accordance with some embodiments, the preservative may include, for example, an antioxidant or an antimicrobial agent, but it is not limited thereto.

In addition, in accordance with some embodiments of the present disclosure, a kit is provided, which includes the aforementioned pharmaceutical composition and an instruction describing the method of use. The kit including the pharmaceutical composition is appropriately packaged. In accordance with some embodiments, the kit may further include a device for administering the pharmaceutical composition (e.g., syringe and needle, nebulizer, or dry powder inhalation device, etc.).

A detailed description is given in the following particular embodiments in order to provide a thorough understanding of the above and other purposes, features and advantages of the present disclosure. However, the scope of the present disclosure is not intended to be limited to the particular embodiments.

Example 1: In Vitro PD-L1 Binding Affinity Test-Flow Cytometry Analysis

Trypsin was used to collect CT-26 cells expressing mouse PD-L1 (mPD-L1) and CHO-K1 cells expressing human PD-L1 (hPD-L1), and the cells were pelleted, washed and resuspended in 100 μl of cell staining buffer (BSA buffer, BD) with approximately $2 \times 10^5$ cells. Then, 100 nmol of the Alexa647-labeled anti-PD-L1 aptamer samples (all the nucleic acid sequences in the present disclosure, including the Alexa647-labeled aptamer, were custom synthesized by Integrated DNA Technologies) were added, and the anti-PD-L1 aptamer samples and suspension of cells were incubated on ice for 60 minutes in the dark. After a single wash in cell staining buffer, the cells were resuspended and analyzed using a FACScan flow cytometer (Becton Dickinson, Oxford, UK).

Figure 1B:
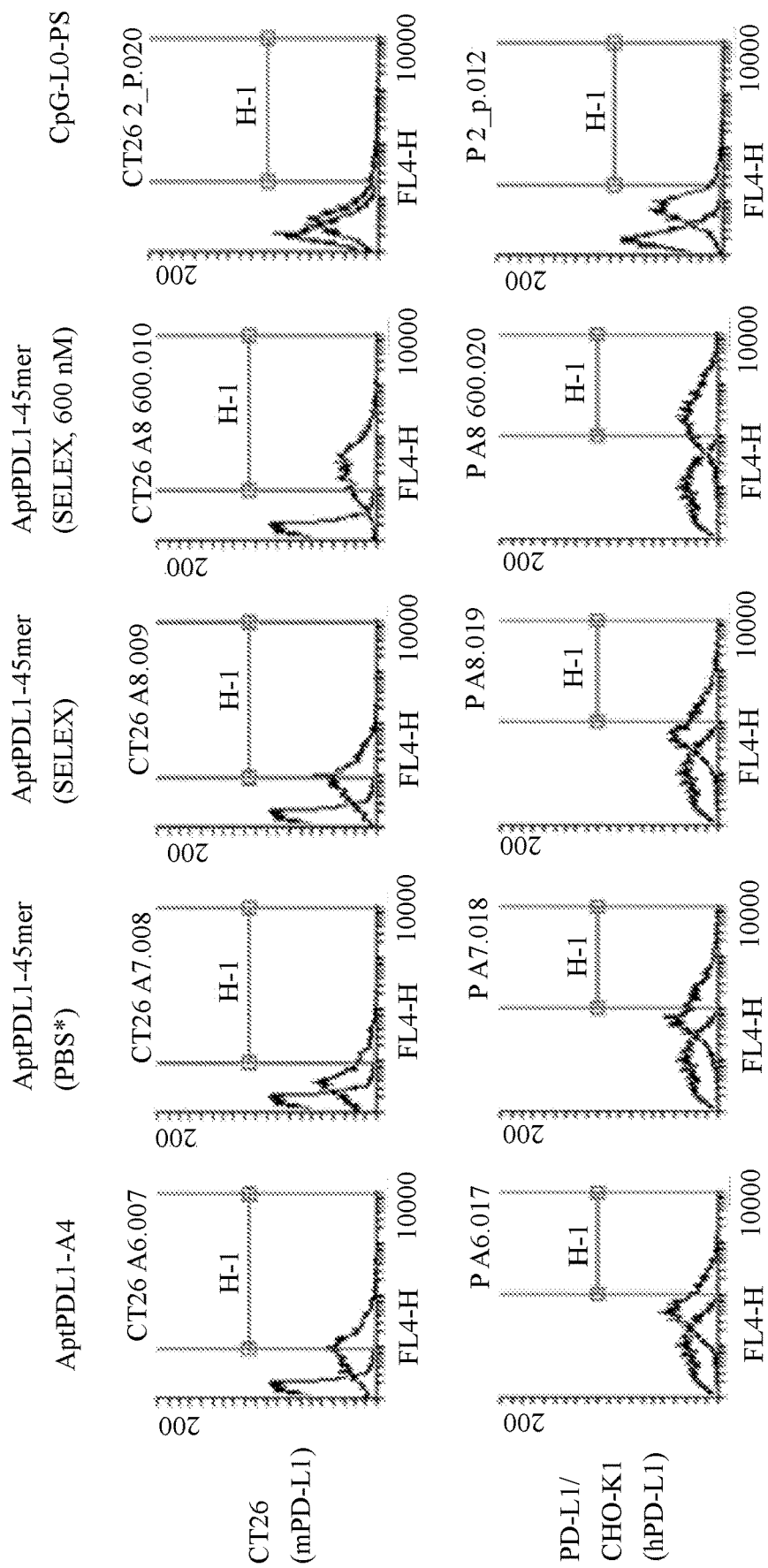
FIG. 1B shows the analysis result of binding affinity for PD-L1 of samples, "AptPDL1-A4", "AptPDL1-45mer (PBS*)", "AptPDL1-45mer (SELEX)" (positive control group), "AptPDL1-45mer (SELEX, 600 nM)" (positive control group) and "CpG-L0-PS", using a flow cytometer in accordance with some embodiments of the present disclosure.

The analysis results of the flow cytometry are shown in FIG. 1A and FIG. 1B. The sample "Unstained" in the figure represents unstained cells and it can be used as a negative control group. The samples "AptPDL1-n05", "AptPDL1-n07", "AptPDL1-1A", "AptPDL1-2A", "AptPDL1-3A" and "AptPDL1-A4" in the figure represent the anti-PD-L1 aptamers of SEQ ID NOs: 4, 5, 6, 7, 8 and 9, respectively, and their concentration all are 100 nM. The sample "AptPDL1-45mer (PBS*)" represents the anti-PD-L1 aptamer of SEQ ID NO: 24, which was not prepared in the cell staining buffer, but was prepared in the modified PBS Buffer (DPBS (Dulbecco's Phosphate-Buffered Saline) containing calcium ions and magnesium ions, added with 1.33 mM KCl) at a concentration of 100 nM, and "AptPDL1-45mer" it can be used as a known control sequence. The sample "AptPDL1-45mer (SELEX)" represents the anti-PD-L1 aptamer of SEQ ID NO: 24 obtained by screening of SELEX technique, and its concentration is 100 nM and it can be used as a positive control group. The sample "AptPDL1-45mer (SELEX, 600 nM)" represents the anti-PD-L1 aptamer of SEQ ID NO: 24 obtained by screening of SELEX technique, and it can be used as a positive control group. The sample "CpG-L0-PS" represents a nucleic acid sequence that does not have affinity for PD-L1, and it can be used as a negative control group.

As shown in FIG. 1A and FIG. 1B, the samples "AptPDL1-n05", "AptPDL1-n07", "AptPDL1-1A", "AptPDL1-2A", "AptPDL1-3A", "AptPDL1-A4" and "AptPDL1-45mer (PBS*, SELEX, 600 nM)" all showed that the peak shifted toward the right, which indicating that they all have binding affinity for PD-L1.

Figure 2:
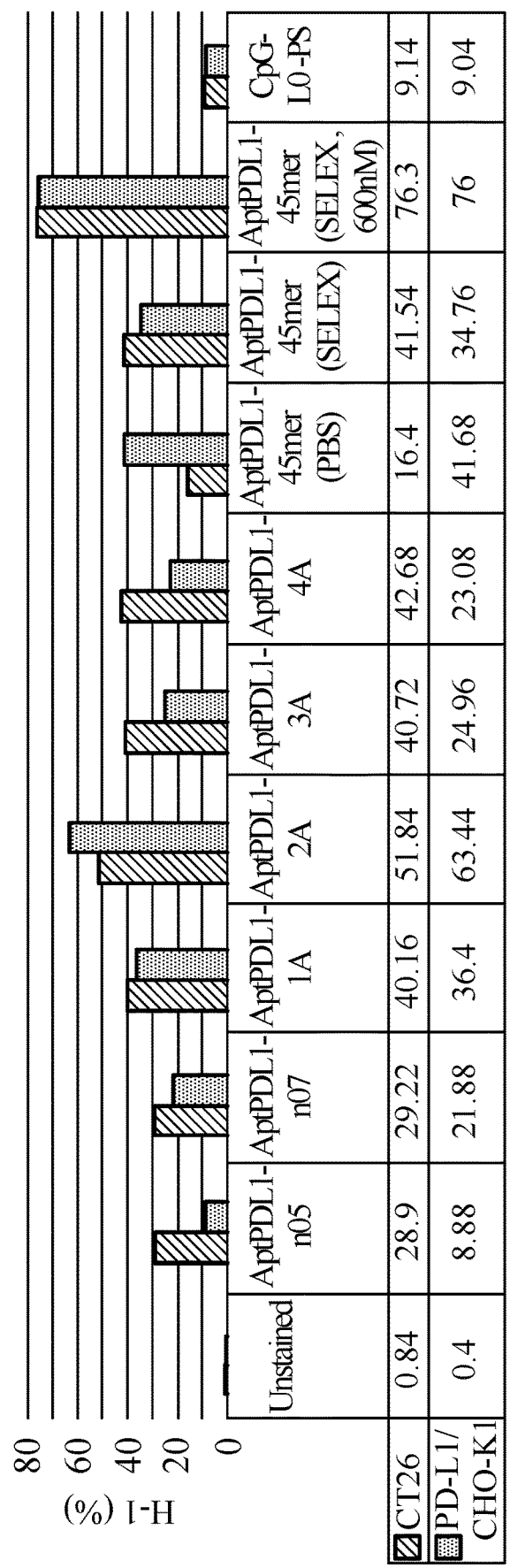
FIG. 2 shows the quantitative data of the experimental results detected by flow cytometer in FIG. 1A and FIG. 1B in accordance with some embodiments of the present disclosure.

Refer to FIG. 2, which shows the quantitative data of the experimental results of the flow cytometry in FIG. 1A and FIG. 1B. As shown in FIG. 2, compared with "CpG-L0-PS" (SEQ ID NO: 10), almost all the samples "AptPDL1-n05" (SEQ ID NO: 4), "AptPDL1-n07" (SEQ ID NO: 5), "AptPDL1-1A" (SEQ ID NO: 6), "AptPDL1-2A" (SEQ ID NO: 7), "AptPDL1-3A" (SEQ ID NO: 8), "AptPDL1-A4" (SEQ ID NO: 9) and "AptPDL1-45mer (PBS*, SELEX, 600 nM)" (SEQ ID NO: 24) showed increased binding affinity for PD-L1.

Example 2: In Vitro PD-L1 Binding Affinity Test-Cell Binding Analysis

The MDA-MB-231 cells expressing PD-L1 were seeded in a 96-well plate (Corning) with a density of $1 \times 10^4$ cells/100 µl/well, and cultured for 48 hours. After removal of medium, the cells were fixed with 50 µl/well of 4% paraformaldehyde (PFA) in phosphate-buffered saline (PBS) for 10 minutes at room temperature. After removal of PFA, 100 µl of 0.1 M glycine in PBS was added to each well to quench the remaining PFA. The 96-well plate was then incubated at room temperature for 10 minutes. The cells were then washed once with PBS and blocked with Super Block (ScyTek Laboratories Inc) for 60 minutes at room temperature. Staining was carried out using varying concentrations of Alexa647-labeled anti-PD-L1 aptamer samples (mixed in PBS) in duplicate wells, and incubated at 37° C. for 45 minutes. Thereafter, the cells were washed four times with PBS, and the fluorescence intensity was measured using Enzyme-Linked Immunosorbent Assay (ELISA plate reader, Tecan, Männedorf, Switzerland) with an excitation wavelength of 670 nm and an emission wavelength of 720 nm.

Figure 3:
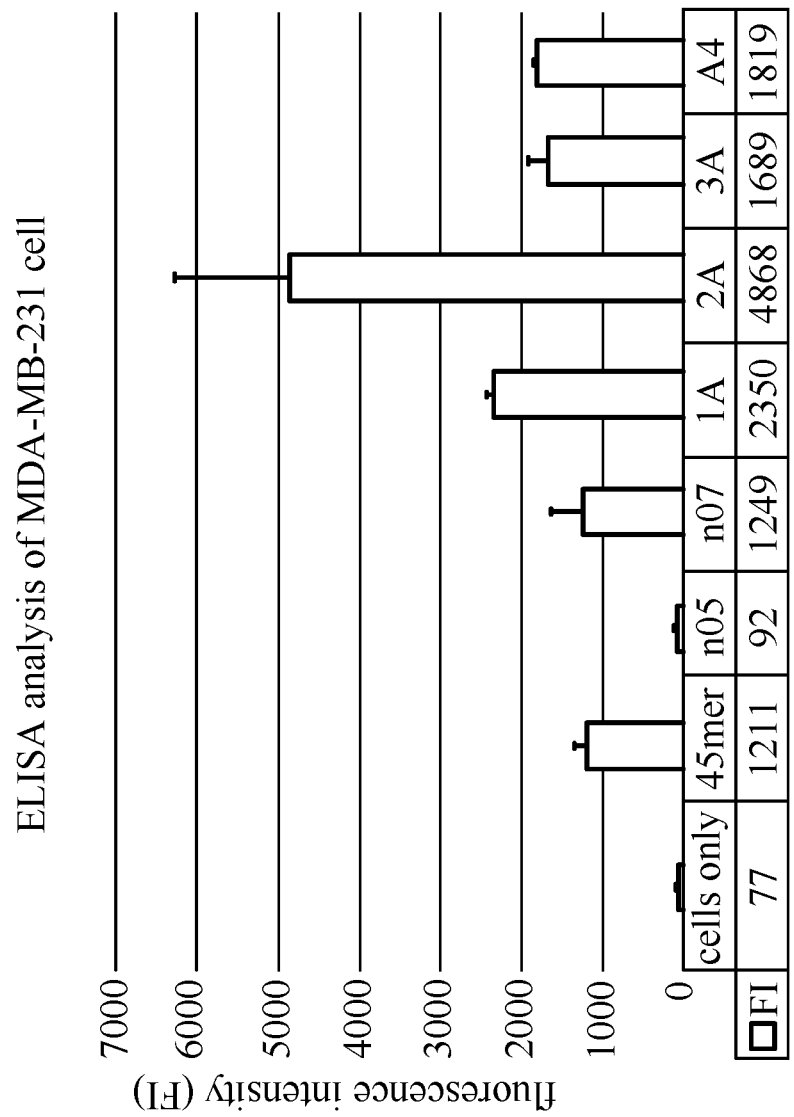
FIG. 3 shows the analysis result of binding affinity for PD-L1 of samples, "cell only" (negative control group), "45mer", "n05", "n07", "1A", "2A", "3A" and "A4", using ELISA technique in accordance with some embodiments of the present disclosure.

The analysis results of ELISA are shown in FIG. 3. The sample "cell only" in the figure represents the cells that do not express PD-L1 and it can be used as a negative control group. The samples "45mer", "n05", "n07", "1A", "2A", "3A" and "A4" in the figure represent the anti-PD-L1 aptamers of SEQ ID NOs: 24, 4, 5, 6, 7, 8 and 9, respectively, and their concentration all are 700 nM, and they were all prepared in the modified PBS buffer (DPBS containing calcium ions and magnesium ions, added with 1.33 mM KCl).

As shown in FIG. 3, the samples "45mer" (AptPDL1-45mer, SEQ ID NO: 24), "n07" (AptPDL1-n07, SEQ ID NO: 5), "1A" (AptPDL1-1A, SEQ ID NO: 6), "2A" (AptPDL1-2A, SEQ ID NO: 7), "3A" (AptPDL1-3A, SEQ ID NO: 8) and "A4" (AptPDL1-A4, SEQ ID NO: 9) all have high fluorescence intensity and have binding affinity for PD-L1.

Example 3: Analysis of TLR9 Activation Ability of Nucleic Acid-Drug Complex-HEK293 Mouse TLR9 Reporting System HEK-Blue cells expressing mouse TLR9 (InvivoGen) were cultured in a complete DMEM medium (Dulbecco's modified Eagle's medium), which was supplemented with 100 µg/ml Normocin, 30 µg/ml Blasticidin, and 100 µg/ml Zeocin (all InvivoGen). HEK-Blue cells contained a secreted alkaline phosphatase (SEAP) reporting system, which produces colorimetric changes after interacting with TLR9.

HEK-Blue Detection mixture (cell culture medium for SEAP detection, InvivoGen) is used to detect the presence of SEAP, which is produced by stimulation of a TLR9 ligand through NF-κB activation. Detection mixture contained nutrients for cell growth and color substrate, whose color will change when it is hydrolyzed by SEAP. When HEK 293 cells expressing mouse TLR9 (InvivoGen) reached 60-80% confluency, they were collected, centrifuged and resuspended in Detection mixture. Cells (72,000) were seeded in each well of a 96-well plate (180 µl). The cells were then treated in combination with 20 µl PBS (unstimulated; as a negative control group), "CpG-L0-PS" (as a positive control group) or nucleic acid-drug complex samples of varying concentrations in PBS in duplicate wells, and incubated for 24 hours at 37° C. in 5% $CO_2$. The plate was read spectrophotometrically by using a multimode plate reader (Tecan, Infinite™ M200 PRO, Männedorf, Switzerland) at a wavelength of 620 nm to 655 nm.

Figure 4:
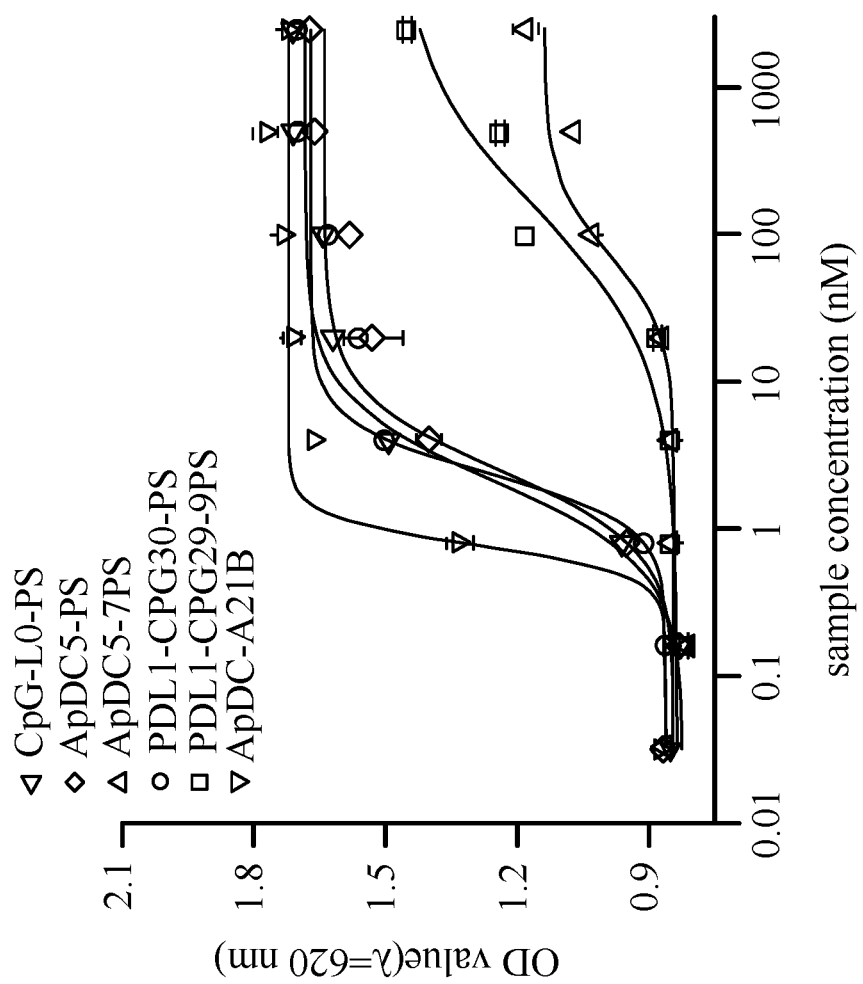
FIG. 4 shows the analysis result of TLR9-activating ability of samples, "CpG-L0-PS", "ApDC5-PS", "ApDC5-7PS", "PDL1-CpG30-PS", "PDL1-CpG29-9PS" and "ApDC-A21B", using the HEK293 mouse TLR9 reporting system in accordance with some embodiments of the present disclosure.
Figure 6B:
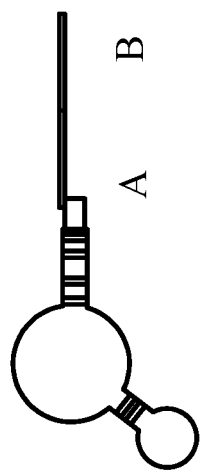
FIGS. 6A-6D are schematic diagrams of the secondary structures of nucleic acid-drug complexes in accordance with some embodiments of the present disclosure.
Figure 6D:
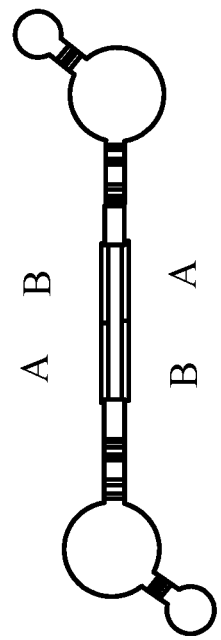
Figure 6A:
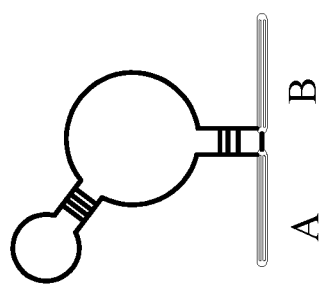
Figure 6C:
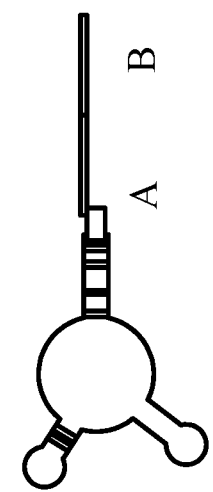

The analysis results of the TLR9 activation ability are shown in FIG. 4. The sample "CpG-L0-PS" in the figure corresponds to SEQ ID NO: 10 (which was not connected with anti-PD-L1 aptamer), and all phosphodiester bonds in the CpG oligonucleotide sequence were modified to phosphorothioate bonds. The sample "ApDC5-PS" corresponds to SEQ ID NO: 25, which represents the pattern that the CpG oligonucleotide sequence was connected to the 5' end of the anti-PD-L1 aptamer sequence, and all phosphodiester bonds in the CpG oligonucleotide sequence were modified to phosphorothioate bonds, and this sample had, for example, the configuration shown in FIG. 6B (in which A and B schematically represent the positions of the first fragment and the second fragment of the CpG oligonucleotides sequence so that the positional relationship between the anti-PD-L1 aptamer and the CpG oligonucleotide sequence can be understood more easily). The sample "ApDC5-7PS" corresponds to SEQ ID NO: 26, which represents the pattern that the CpG oligonucleotide sequence was connected to the 5' end of the anti-PD-L1 aptamer sequence, and only part of the phosphodiester bonds in the CpG oligonucleotide sequence were modified to phosphorothioate bond, and this sample had, for example, the configuration shown in FIG. 6D. The sample "PDL1-CpG30-PS" corresponds to SEQ ID NO: 27, which represents the pattern that the CpG oligonucleotide sequence was connected to the 3' end of the anti-PD-L1 aptamer sequence, and all phosphodiester bonds in the CpG oligonucleotide sequence were modified to phosphorothioate bond, and this sample had, for example, the configuration shown in FIG. 6C. The sample "PDL1-CpG29-9PS" corresponds to SEQ ID NO: 28, which represents the pattern that the CpG oligonucleotide sequence was connected to the 3' end of the anti-PD-L1 aptamer sequence, and only part of the phosphodiester bonds in the CpG oligonucleotide sequence were modified to phosphorothioate bond, and this sample had, for example, the configuration shown in FIG. 6D. The sample "ApDC-A21B" corresponds to SEQ ID NO: 31, which represents the pattern that the anti-PD-L1 aptamer sequence was inserted into the CpG oligonucleotide sequence, and all phosphodiester bonds in the CpG oligonucleotide sequence were modified to phosphorothioate bonds, and this sample had, for example, the configuration shown in FIG. 6A.

According to the results shown in FIG. 4, the $EC_{50}$ value of the sample "CpG-L0-PS" (SEQ ID NO: 10) was 2.09 nM, the $EC_{50}$ value of the sample "ApDC5-PS" (SEQ ID NO: 25) was 2.48 nM, the $EC_{50}$ value of the sample ApDC5-7PS (SEQ ID NO: 26) was 72.23 nM, the $EC_{50}$ value of the sample "PDL1-CpG30-PS" (SEQ ID NO: 27) was 2.36 nM, the $EC_{50}$ value of the sample "PDL1-CpG29-9PS" (SEQ ID NO: 28) was 148.82 nM, and the $EC_{50}$ value of the sample "ApDC-A21B" (SEQ ID NO: 31) was 0.77 nM. Compared with other samples, the sample "ApDC-A21B" (SEQ ID NO: 31) had the lowest $EC_{50}$ value and had an improved TLR9 activation ability.

It can be seen that, compared with the patterns that the CpG oligonucleotide sequence was connected to the 5' or 3' end of the anti-PD-L1 aptamer sequence, the nucleic acid-drug complex that the anti-PD-L1 aptamer sequence was inserted into the CpG oligonucleotide sequence had better TLR9 activation ability. In addition, since only part of the phosphodiester bonds in the CpG oligonucleotide sequence being modified to phosphorothioate bonds is likely to form a complementary double-stranded structure, the nucleic acid-drug complex of such pattern had decreased TLR9 activation ability.

Figure 5:
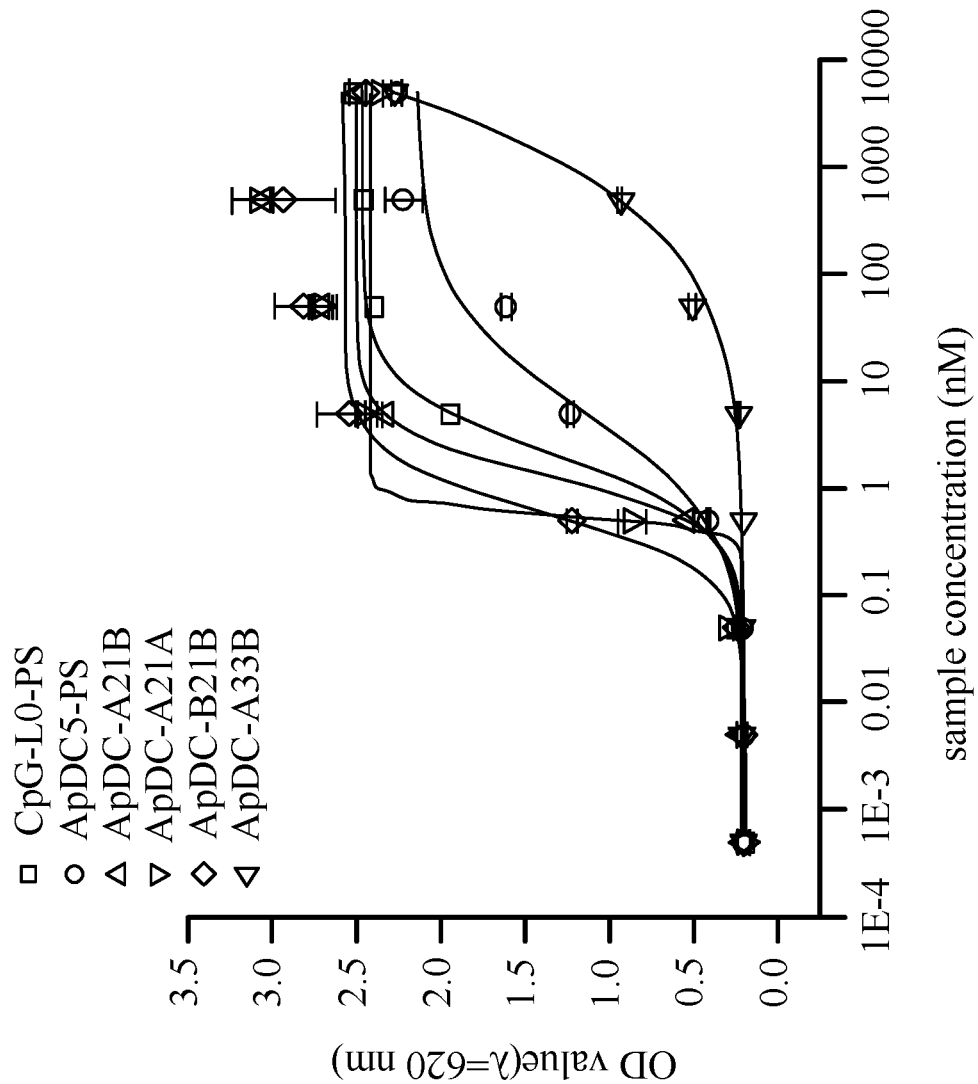
FIG. 5 shows the analysis result of TLR9-activating ability of samples, "CpG-L0-PS", "ApDC5-PS", "ApDC-A21B", "ApDC-A21A", "ApDC-B21B" and "ApDC-A33B", using the HEK293 mouse TLR9 reporting system in accordance with some embodiments of the present disclosure.

Next, refer to FIG. 5, which shows the analysis results of the TLR9 activation ability of the nucleic acid-drug complex in accordance with another embodiment. The experimental content is substantially the same as that of FIG. 4. The sample "CpG-L0-PS" in FIG. 5 corresponds to SEQ ID NO: 10 (which was not connected with anti-PD-L1 aptamer), and all phosphodiester bonds in the CpG oligonucleotide sequence were modified to phosphorothioate bonds. The sample "ApDC5-PS" corresponds SEQ ID NO: 25, which represents the pattern that the CpG oligonucleotide sequence was connected to the 5' end of the anti-PD-L1 aptamer sequence, and all phosphodiester bonds in the CpG oligonucleotide sequence were modified to phosphorothioate bonds, and this sample had, for example, the configuration shown in FIG. 6B. The sample "ApDC-A21B" corresponds to SEQ ID NO: 31, which represents the pattern that the anti-PD-L1 aptamer sequence was inserted into the CpG oligonucleotide sequence, and all phosphodiester bonds in the CpG oligonucleotide sequence were modified to phosphorothioate bonds, and this sample had, for example, the configuration shown in FIG. 6A. The sample "ApDC-A21A" corresponds to SEQ ID NO: 32, which represents the pattern that the anti-PD-L1 aptamer sequence was inserted into the CpG oligonucleotide sequence, and all phosphodiester bonds in the CpG oligonucleotide sequence were modified to phosphorothioate bonds, and this sample had the configuration similar to that shown in FIG. 6A, but the sequences of fragment A and fragment B were the same. The sample "ApDC-B21B" corresponds to SEQ ID NO: 33, which represents the pattern that the anti-PD-L1 aptamer sequence was inserted into the CpG oligonucleotide sequence, and all phosphodiester bonds in the CpG oligonucleotide sequence were modified to phosphorothioate bonds, and this sample had the configuration similar to that shown in FIG. 6A, but the sequences of fragment A and fragment B were the same. The sample "ApDC-A33B" corresponds to SEQ ID NO: 30, which represents the pattern that the anti-PD-L1 aptamer sequence was inserted into the CpG oligonucleotide sequence, and only part of the phosphodiester bonds in the CpG oligonucleotide sequence were modified to phosphorothioate bond.

According to the results shown in FIG. 5, the $EC_{50}$ value of the sample "CpG-L0-PS" (SEQ ID NO: 10) was 2.1 nM, the $EC_{50}$ value of the sample "ApDC5-PS" (SEQ ID NO: 25) was 5.5 nM, the $EC_{50}$ value of the sample "ApDC-A21B" (SEQ ID NO: 31) was 1.3 nM, the $EC_{50}$ value of the sample "ApDC-A21A" (SEQ ID NO: 32) was 0.6 nM, the $EC_{50}$ value of the sample "ApDC-B21B" (SEQ ID NO: 33) was 0.6 nM, and the $EC_{50}$ value of the sample "ApDC-A33B" (SEQ ID NO: 30) was 16380 nM.

Compared with the sample "ApDC5-PS" (SEQ ID NO: 25), the samples "ApDC-A21B" (SEQ ID NO: 31), "ApDC-A21A" (SEQ ID NO: 32) and "ApDC-B21B" (SEQ ID NO: 33), in which the anti-PD-L1 aptamer sequence was inserted into the CpG oligonucleotide sequence, have lower $EC_{50}$ values, i.e. improved TLR9 activation ability. In addition, compared with the pattern that only part of the phosphodiester bonds in the CpG oligonucleotide sequence were modified to phosphorothioate bonds, the pattern that all phosphodiester bonds in the CpG oligonucleotide sequence were modified to phosphorothioate bonds also had better TLR9 activation ability.

Example 4: In Vivo Anti-Tumor Efficacy Analysis of Nucleic Acid-Drug Complex in Animal Models The 4T1 murine breast cancer syngeneic tumor model was used for the study of in vivo anti-tumor efficacy. BALB/c mice were implanted subcutaneously with 4T1 ($5×10^5$ cells). Tumor size was measured using a caliper and converted into tumor volume using the following formula: V=LS2/2 (where L is the longest diameter and S is the shortest diameter). The mice were randomly divided into groups (n=4~5), and the drug was administered when the tumor volume reached 100-200 $mm^3$. Anti-mouse PD-L1 antibody (PDL1 mAb, InVivoPlus anti-mouse PD-L1, BioXCell) was injected intraperitoneally twice a week. The CpG oligonucleotides (SEQ ID NO: 10) and the anti-PD-L1 aptamers (SEQ ID NO: 1) (combined use, labeled as AptPDL1+CpG), and the nucleic acid-drug complex of the anti-PD-L1 aptamer being conjugated to the CpG oligonucleotide sequence (SEQ ID NO: 25) (labeled as ApDC5-PS) were injected intravenously twice a week. The anti-tumor efficacy is determined by the percentage of tumor growth inhibition (TGI). The calculation method of TGI was [1−(final tumor volume−initial tumor volume of treatment group)/(final tumor volume−initial tumor volume of vehicle group)]×100%.

Figure 7:
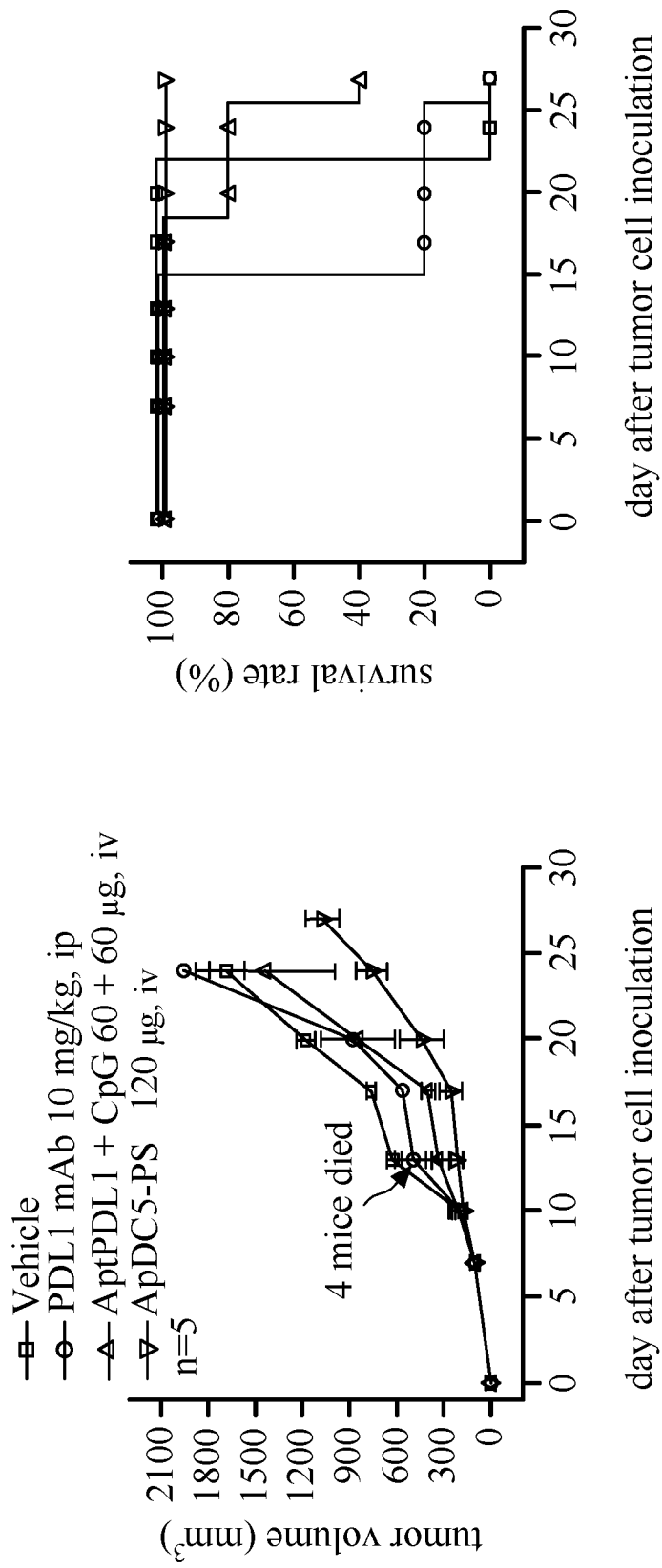
FIG. 7 shows the influence of administering samples, "Vehicle" (negative control group), "PDL1 mAb", "AptPDL1+CpG" and "ApDC5-PS", on the tumor volume and survival rate of mouse using the 4T1 murine breast cancer syngeneic tumor model in accordance with some embodiments of the present disclosure.

According to the results shown in FIG. 7, the tumor volume treated with the sample "ApDC5-PS" (SEQ ID NO: 25) was significantly decreased, and its anti-tumor efficacy was better than the pattern of combined use of CpG oligonucleotides and anti-PD-L1 aptamers (AptPDL1+CpG), and was also better than the pattern of injecting anti-mouse PD-L1 antibody (PDL1 mAb) alone. In addition, the survival rate of mice injected with the sample "ApDC5-PS" was greatly improved, and the survival rate was still 100% after 25 days after tumor cell inoculation.

Figure 8:
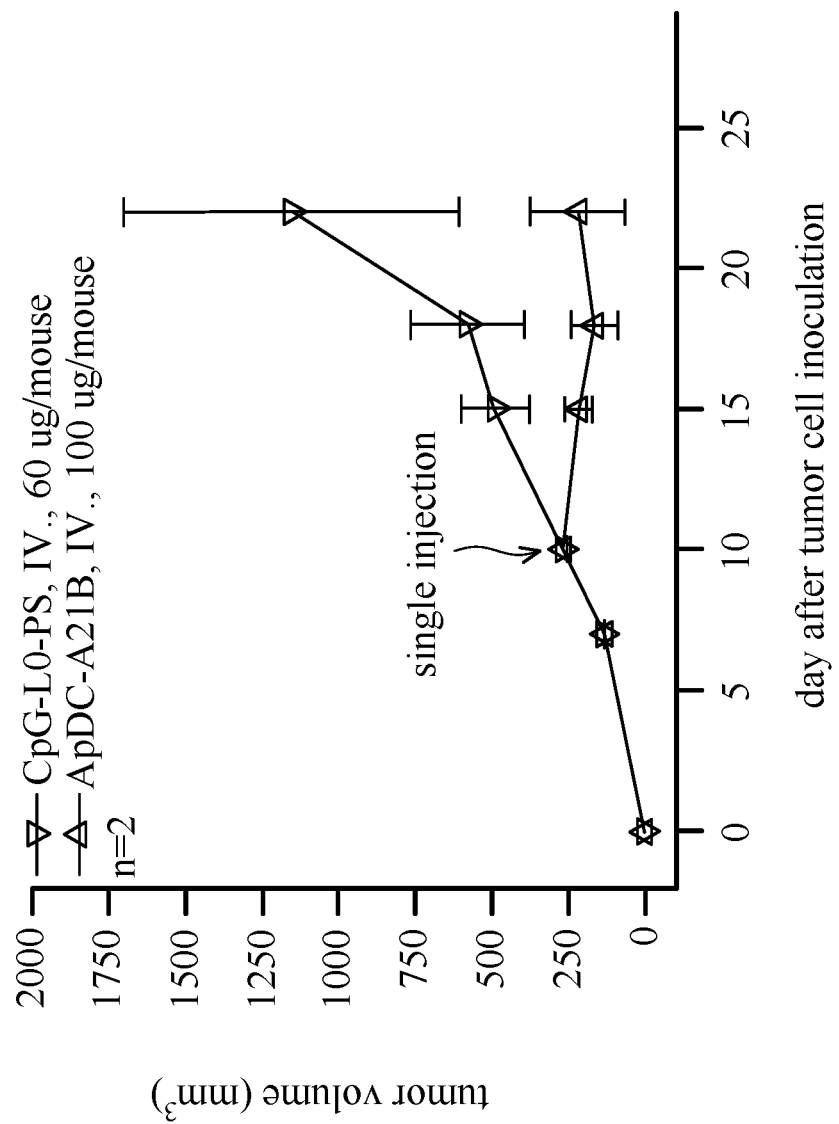
FIG. 8 shows the influence of administering samples, "CpG-L0-PS" and "ApDC-A21B", on the tumor volume of mouse using the 4T1 murine breast cancer syngeneic tumor model in accordance with some embodiments of the present disclosure.

Furthermore, FIG. 8 shows the results of the anti-tumor efficacy analysis of the nucleic acid-drug complex in accordance with another embodiment, and the experimental content is substantially the same as that of FIG. 7. The sample "CpG-L0-PS" in FIG. 8 corresponds to SEQ ID NO: 10 (which was not connected with anti-PD-L1 aptamer). The sample "ApDC-A21B" corresponds to SEQ ID NO: 31, which is the pattern that the anti-PD-L1 aptamer sequence was inserted into the CpG oligonucleotide sequence. As shown in FIG. 8, compared with the sample "CpG-L0-PS", the sample "ApDC-A21B" had better anti-tumor efficacy and improved medical efficacy.

As described above, the novel nucleic acid-drug complex provided in the embodiments of the present disclosure combines CpG oligonucleotide sequence and anti-PD-L1 aptamer, which has tumor targetability and immune checkpoint-blocking activity, and can increase the accumulation of nucleic acid-drug complexes in tumors and the immune cytotoxicity in tumor microenvironment. In addition, the nucleic acid-drug complex has the ability to stimulate the activation of a variety of immune cells, and can increase the activation and aggregation of immune cells in tumor microenvironment. Moreover, the nucleic acid-drug complexes provided in the embodiments of the present disclosure have better anti-tumor efficacy than simply combining the uses of CpG oligonucleotides and anti-PD-L1 aptamers.

Although some embodiments of the present disclosure and their advantages have been described in detail, it should be understood that various changes, substitutions and alterations can be made herein without departing from the spirit and scope of the disclosure as defined by the appended claims. In addition, each claim constitutes an individual embodiment, and the claimed scope of the present disclosure also includes the combinations of the claims and embodiments. The scope of protection of the present disclosure is subject to the definition of the scope of the appended claims.

---

What is claimed is:

1. A nucleic acid-drug complex, comprising:
   a nucleic acid sequence of an anti-PD-L1 aptamer, which binds to PD-L1; and
   a CpG oligonucleotide sequence, which binds to TLR9 receptor and is used to activate TLR9, wherein the CpG oligonucleotide sequence consists of a first fragment and a second fragment, wherein the first fragment is different from the second fragment, and wherein the nucleic acid sequence of the anti-PD-L1 aptamer is inserted between the first fragment and the second fragment of the CpG oligonucleotide sequence,
   wherein a ratio of a length of the first fragment of the CpG oligonucleotide sequence to a length of the second fragment of the CpG oligonucleotide sequence is in a range from 1:10 to 10:1, and a total length of the first fragment and the second fragment is 15 to 40 nucleotides.

2. The nucleic acid-drug complex as claimed in claim 1, wherein the CpG oligonucleotide sequence has at least 85% similarity to the nucleic acid sequence shown in any one of SEQ ID NOs: 10 to 21 and 23.

3. The nucleic acid-drug complex as claimed in claim 2, wherein the CpG oligonucleotide sequence consists of any one of SEQ ID NOs: 10 to 21 and 23.

4. The nucleic acid-drug complex as claimed in claim 1, wherein the CpG oligonucleotide sequence includes a phosphorothioate bond.

5. The nucleic acid-drug complex as claimed in claim 4, wherein 70% to 100% of phosphodiester bonds in the CpG oligonucleotide sequence are phosphorothioate bonds.

6. The nucleic acid-drug complex as claimed in claim 5, wherein 80% to 100% of the phosphodiester bonds in the CpG oligonucleotide sequence are phosphorothioate bonds.

7. The nucleic acid-drug complex as claimed in claim 1, which consists of a nucleic acid sequence shown in any one of SEQ ID NOs: 29 to 34.

8. A method for treating cancer, comprising
   administering the nucleic acid-drug complex as claimed in claim 1 to a subject in need thereof.

9. The method as claimed in claim 8, wherein the cancer comprises colon cancer, breast cancer, lung cancer, pancreatic cancer, liver cancer, stomach cancer, esophageal cancer, head and neck squamous cell carcinoma, prostate cancer, bladder cancer, lymphoma, gallbladder cancer, kidney cancer, blood cancer, colorectal cancer, multiple myeloma, ovarian cancer, cervical cancer or glioma.

10. A pharmaceutical composition, comprising the nucleic acid-drug complex as claimed in claim 1 and a pharmaceutically acceptable carrier.

11. The pharmaceutical composition as claimed in claim 10, which is used for treatment of cancer.

12. The pharmaceutical composition as claimed in claim 10, which is administered by intravenous injection, intratumoral injection or subcutaneous injection.

13. A kit, comprising the pharmaceutical composition as claimed in claim 10.

* * * * *

SEQUENCE LISTING

```
<160> NUMBER OF SEQ ID NOS: 34

<210> SEQ ID NO 1
<211> LENGTH: 30
<212> TYPE: DNA
<213> ORGANISM: Artificial Sequence
<220> FEATURE:
<223> OTHER INFORMATION: anti-PD-L1 aptamer

<400> SEQUENCE: 1
cacatcaact cattgataga caatgcgtcc                                       30

<210> SEQ ID NO 2
<211> LENGTH: 35
<212> TYPE: DNA
<213> ORGANISM: Artificial Sequence
<220> FEATURE:
<223> OTHER INFORMATION: anti-PD-L1 aptamer

<400> SEQUENCE: 2
ccacatcaac tcattgatag acaatgcgtc caccg                                 35

<210> SEQ ID NO 3
<211> LENGTH: 21
<212> TYPE: DNA
<213> ORGANISM: Artificial Sequence
<220> FEATURE:
<223> OTHER INFORMATION: anti-PD-L1 aptamer

<400> SEQUENCE: 3
actcattgat agacaatgcg t                                                21

<210> SEQ ID NO 4
<211> LENGTH: 21
<212> TYPE: DNA
<213> ORGANISM: Artificial Sequence
<220> FEATURE:
<223> OTHER INFORMATION: anti-PD-L1 aptamer

<400> SEQUENCE: 4
agcgattgat agacaatcgc t                                                21

<210> SEQ ID NO 5
<211> LENGTH: 26
<212> TYPE: DNA
<213> ORGANISM: Artificial Sequence
<220> FEATURE:
<223> OTHER INFORMATION: anti-PD-L1 aptamer
```

<400> SEQUENCE: 5
atgaactcat tcatacacaa tgcgtg    26

<210> SEQ ID NO 6
<211> LENGTH: 32
<212> TYPE: DNA
<213> ORGANISM: Artificial Sequence
<220> FEATURE:
<223> OTHER INFORMATION: anti-PD-L1 aptamer

<400> SEQUENCE: 6
gttgtttttt cactcattga tagacaatgc gt    32

<210> SEQ ID NO 7
<211> LENGTH: 30
<212> TYPE: DNA
<213> ORGANISM: Artificial Sequence
<220> FEATURE:
<223> OTHER INFORMATION: anti-PD-L1 aptamer

<400> SEQUENCE: 7
agttatgctt tccccctctt tgatagacaa    30

<210> SEQ ID NO 8
<211> LENGTH: 31
<212> TYPE: DNA
<213> ORGANISM: Artificial Sequence
<220> FEATURE:
<223> OTHER INFORMATION: anti-PD-L1 aptamer

<400> SEQUENCE: 8
gaacaaaggt attagacatc ttgatagaca a    31

<210> SEQ ID NO 9
<211> LENGTH: 30
<212> TYPE: DNA
<213> ORGANISM: Artificial Sequence
<220> FEATURE:
<223> OTHER INFORMATION: anti-PD-L1 aptamer

<400> SEQUENCE: 9
actcattgat agacaatgcg tgcccgcagc    30

<210> SEQ ID NO 10
<211> LENGTH: 30
<212> TYPE: DNA
<213> ORGANISM: Artificial Sequence
<220> FEATURE:
<223> OTHER INFORMATION: CpG sequence
<220> FEATURE:
<221> NAME/KEY: misc_difference
<222> LOCATION: (1)..(29)
<223> OTHER INFORMATION: phosphorothioate bond

<400> SEQUENCE: 10
tcgaacgttc gaacgttcga acgttcgaat    30

<210> SEQ ID NO 11
<211> LENGTH: 20
<212> TYPE: DNA
<213> ORGANISM: mouse
<220> FEATURE:
<221> NAME/KEY: misc_difference
<222> LOCATION: (1)..(19)
<223> OTHER INFORMATION: phosphorothioate bond

```
<400> SEQUENCE: 11
tccatgacgt tcctgacgtt                                             20

<210> SEQ ID NO 12
<211> LENGTH: 24
<212> TYPE: DNA
<213> ORGANISM: Homo sapiens
<220> FEATURE:
<221> NAME/KEY: misc_difference
<222> LOCATION: (1)..(23)
<223> OTHER INFORMATION: phosphorothioate bond

<400> SEQUENCE: 12
tcgtcgtttt gtcgttttgt cgtt                                        24

<210> SEQ ID NO 13
<211> LENGTH: 20
<212> TYPE: DNA
<213> ORGANISM: mouse
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: misc_difference
<222> LOCATION: (15)..(19)
<223> OTHER INFORMATION: phosphorothioate bond

<400> SEQUENCE: 13
ggggtcaacg ttgagggggg                                             20

<210> SEQ ID NO 14
<211> LENGTH: 20
<212> TYPE: DNA
<213> ORGANISM: mouse
<220> FEATURE:
<221> NAME/KEY: misc_difference
<222> LOCATION: (1)..(19)
<223> OTHER INFORMATION: phosphorothioate bond

<400> SEQUENCE: 14
tccatgacgt tcctgatgct                                             20

<210> SEQ ID NO 15
<211> LENGTH: 22
<212> TYPE: DNA
<213> ORGANISM: Bovine
<220> FEATURE:
<221> NAME/KEY: misc_difference
<222> LOCATION: (1)..(21)
<223> OTHER INFORMATION: phosphorothioate bond

<400> SEQUENCE: 15
tcgtcgttgt cgttttgtcg tt                                          22

<210> SEQ ID NO 16
<211> LENGTH: 23
<212> TYPE: DNA
<213> ORGANISM: Homo sapiens
<220> FEATURE:
<221> NAME/KEY: misc_difference
<222> LOCATION: (1)..(22)
<223> OTHER INFORMATION: phosphorothioate bond

<400> SEQUENCE: 16
tcgacgttcg tcgttcgtcg ttc                                         23
```

```
<210> SEQ ID NO 17
<211> LENGTH: 22
<212> TYPE: DNA
<213> ORGANISM: Homo sapiens
<220> FEATURE:
<221> NAME/KEY: misc_difference
<222> LOCATION: (1)..(21)
<223> OTHER INFORMATION: phosphorothioate bond

<400> SEQUENCE: 17
tgactgtgaa cgttcgagat ga                                          22

<210> SEQ ID NO 18
<211> LENGTH: 26
<212> TYPE: DNA
<213> ORGANISM: unknown
<220> FEATURE:
<223> OTHER INFORMATION: multi-species
<220> FEATURE:
<221> NAME/KEY: misc_difference
<222> LOCATION: (1)..(25)
<223> OTHER INFORMATION: phosphorothioate bond

<400> SEQUENCE: 18
tcgcgacgtt cgcccgacgt tcggta                                      26

<210> SEQ ID NO 19
<211> LENGTH: 29
<212> TYPE: DNA
<213> ORGANISM: unknown
<220> FEATURE:
<223> OTHER INFORMATION: multi-species
<220> FEATURE:
<221> NAME/KEY: misc_difference
<222> LOCATION: (1)..(28)
<223> OTHER INFORMATION: phosphorothioate bond

<400> SEQUENCE: 19
tcgcgaacgt tcgccgcgtt cgaacgcgg                                   29

<210> SEQ ID NO 20
<211> LENGTH: 21
<212> TYPE: DNA
<213> ORGANISM: Homo sapiens
<220> FEATURE:
<221> NAME/KEY: misc_difference
<222> LOCATION: (1)..(20)
<223> OTHER INFORMATION: phosphorothioate bond

<400> SEQUENCE: 20
tcgtcgaacg ttcgagatga t                                           21

<210> SEQ ID NO 21
<211> LENGTH: 25
<212> TYPE: DNA
<213> ORGANISM: Homo sapiens
<220> FEATURE:
<221> NAME/KEY: misc_difference
<222> LOCATION: (1)..(24)
<223> OTHER INFORMATION: phosphorothioate bond

<400> SEQUENCE: 21
tcgaacgttc gaacgttcga acgtt                                       25

<210> SEQ ID NO 22
<211> LENGTH: 30
<212> TYPE: DNA
<213> ORGANISM: Artificial Sequence
<220> FEATURE:
```

```
<223> OTHER INFORMATION: CpG sequence
<220> FEATURE:
<221> NAME/KEY: misc_difference
<222> LOCATION: (1)..(29)
<223> OTHER INFORMATION: phosphorothioate bond

<400> SEQUENCE: 22
tcgaacgttc gaacgtcgaa cgttcgaacg                              30

<210> SEQ ID NO 23
<211> LENGTH: 30
<212> TYPE: DNA
<213> ORGANISM: Artificial Sequence
<220> FEATURE:
<223> OTHER INFORMATION: CpG sequence
<220> FEATURE:
<221> NAME/KEY: misc_difference
<222> LOCATION: (1)..(29)
<223> OTHER INFORMATION: phosphorothioate bond

<400> SEQUENCE: 23
ttcgaacgtt cgaatttcga acgttcgaat                              30

<210> SEQ ID NO 24
<211> LENGTH: 45
<212> TYPE: DNA
<213> ORGANISM: Artificial Sequence
<220> FEATURE:
<223> OTHER INFORMATION: anti-PD-L1 aptamer

<400> SEQUENCE: 24
acgggccaca tcaactcatt gatagacaat gcgtccactg cccgt             45

<210> SEQ ID NO 25
<211> LENGTH: 60
<212> TYPE: DNA
<213> ORGANISM: Artificial Sequence
<220> FEATURE:
<223> OTHER INFORMATION: anti-PD-L1 aptamer-CpG sequence
<220> FEATURE:
<221> NAME/KEY: misc_difference
<222> LOCATION: (1)..(29)
<223> OTHER INFORMATION: phosphorothioate bond

<400> SEQUENCE: 25
tcgaacgttc gaacgttcga acgttcgaat cacatcaact cattgataga caatgcgtcc  60

<210> SEQ ID NO 26
<211> LENGTH: 60
<212> TYPE: DNA
<213> ORGANISM: Artificial Sequence
<220> FEATURE:
<223> OTHER INFORMATION: anti-PD-L1 aptamer-CpG sequence
<220> FEATURE:
<221> NAME/KEY: misc_difference
<222> LOCATION: (2)..(2)
<223> OTHER INFORMATION: phosphorothioate bond
<220> FEATURE:
<221> NAME/KEY: misc_difference
<222> LOCATION: (6)..(6)
<223> OTHER INFORMATION: phosphorothioate bond
<220> FEATURE:
<221> NAME/KEY: misc_difference
<222> LOCATION: (10)..(10)
<223> OTHER INFORMATION: phosphorothioate bond
<220> FEATURE:
<221> NAME/KEY: misc_difference
<222> LOCATION: (14)..(14)
<223> OTHER INFORMATION: phosphorothioate bond
<220> FEATURE:
<221> NAME/KEY: misc_difference
```

```
<222> LOCATION: (18)..(18)
<223> OTHER INFORMATION: phosphorothioate bond
<220> FEATURE:
<221> NAME/KEY: misc_difference
<222> LOCATION: (22)..(22)
<223> OTHER INFORMATION: phosphorothioate bond
<220> FEATURE:
<221> NAME/KEY: misc_difference
<222> LOCATION: (26)..(26)
<223> OTHER INFORMATION: phosphorothioate bond

<400> SEQUENCE: 26
tcgaacgttc gaacgttcga acgttcgaat cacatcaact cattgataga caatgcgtcc    60

<210> SEQ ID NO 27
<211> LENGTH: 60
<212> TYPE: DNA
<213> ORGANISM: Artificial Sequence
<220> FEATURE:
<223> OTHER INFORMATION: anti-PD-L1 aptamer-CpG sequence
<220> FEATURE:
<221> NAME/KEY: misc_difference
<222> LOCATION: (31)..(59)
<223> OTHER INFORMATION: phosphorothioate bond

<400> SEQUENCE: 27
cacatcaact cattgataga caatgcgtcc tcgaacgttc gaacgttcga acgttcgaat    60

<210> SEQ ID NO 28
<211> LENGTH: 60
<212> TYPE: DNA
<213> ORGANISM: Artificial Sequence
<220> FEATURE:
<223> OTHER INFORMATION: anti-PD-L1 aptamer-CpG sequence
<220> FEATURE:
<221> NAME/KEY: misc_difference
<222> LOCATION: (33)..(33)
<223> OTHER INFORMATION: phosphorothioate bond
<220> FEATURE:
<221> NAME/KEY: misc_difference
<222> LOCATION: (37)..(37)
<223> OTHER INFORMATION: phosphorothioate bond
<220> FEATURE:
<221> NAME/KEY: misc_difference
<222> LOCATION: (41)..(41)
<223> OTHER INFORMATION: phosphorothioate bond
<220> FEATURE:
<221> NAME/KEY: misc_difference
<222> LOCATION: (45)..(45)
<223> OTHER INFORMATION: phosphorothioate bond
<220> FEATURE:
<221> NAME/KEY: misc_difference
<222> LOCATION: (49)..(49)
<223> OTHER INFORMATION: phosphorothioate bond
<220> FEATURE:
<221> NAME/KEY: misc_difference
<222> LOCATION: (53)..(53)
<223> OTHER INFORMATION: phosphorothioate bond
<220> FEATURE:
<221> NAME/KEY: misc_difference
<222> LOCATION: (57)..(59)
<223> OTHER INFORMATION: phosphorothioate bond

<400> SEQUENCE: 28
cacatcaact cattgataga caatgcgtcc ttcgaacgtt cgaacgttcg aacgttcgaa    60

<210> SEQ ID NO 29
<211> LENGTH: 60
<212> TYPE: DNA
<213> ORGANISM: Artificial Sequence
<220> FEATURE:
<223> OTHER INFORMATION: anti-PD-L1 aptamer-CpG sequence
<220> FEATURE:
```

```
<221> NAME/KEY: misc_difference
<222> LOCATION: (1)..(14)
<223> OTHER INFORMATION: phosphorothioate bond
<220> FEATURE:
<221> NAME/KEY: misc_difference
<222> LOCATION: (46)..(59)
<223> OTHER INFORMATION: phosphorothioate bond

<400> SEQUENCE: 29
tcgaacgttc gaacgcacat caactcattg atagacaatg cgtccttcga acgttcgaat    60

<210> SEQ ID NO 30
<211> LENGTH: 67
<212> TYPE: DNA
<213> ORGANISM: Artificial Sequence
<220> FEATURE:
<223> OTHER INFORMATION: anti-PD-L1 aptamer-CpG sequence
<220> FEATURE:
<221> NAME/KEY: misc_difference
<222> LOCATION: (1)..(2)
<223> OTHER INFORMATION: phosphorothioate bond
<220> FEATURE:
<221> NAME/KEY: misc_difference
<222> LOCATION: (66)..(66)
<223> OTHER INFORMATION: phosphorothioate bond

<400> SEQUENCE: 30
tttcgaacgt tcgaacgcca catcaactca ttgatagaca atgcgtccac cgttcgaacg    60
ttcgatt                                                              67

<210> SEQ ID NO 31
<211> LENGTH: 51
<212> TYPE: DNA
<213> ORGANISM: Artificial Sequence
<220> FEATURE:
<223> OTHER INFORMATION: anti-PD-L1 aptamer-CpG sequence
<220> FEATURE:
<221> NAME/KEY: misc_difference
<222> LOCATION: (1)..(14)
<223> OTHER INFORMATION: phosphorothioate bond
<220> FEATURE:
<221> NAME/KEY: misc_difference
<222> LOCATION: (37)..(50)
<223> OTHER INFORMATION: phosphorothioate bond

<400> SEQUENCE: 31
tcgaacgttc gaacgactca ttgatagaca atgcgtttcg aacgttcgaa t             51

<210> SEQ ID NO 32
<211> LENGTH: 51
<212> TYPE: DNA
<213> ORGANISM: Artificial Sequence
<220> FEATURE:
<223> OTHER INFORMATION: anti-PD-L1 aptamer-CpG sequence
<220> FEATURE:
<221> NAME/KEY: misc_difference
<222> LOCATION: (1)..(14)
<223> OTHER INFORMATION: phosphorothioate bond
<220> FEATURE:
<221> NAME/KEY: misc_difference
<222> LOCATION: (37)..(50)
<223> OTHER INFORMATION: phosphorothioate bond

<400> SEQUENCE: 32
tcgaacgttc gaacgactca ttgatagaca atgcgttcga acgttcgaac g             51

<210> SEQ ID NO 33
<211> LENGTH: 50
<212> TYPE: DNA
<213> ORGANISM: Artificial Sequence
```

```
<220> FEATURE:
<223> OTHER INFORMATION: anti-PD-L1 aptamer-CpG sequence
<220> FEATURE:
<221> NAME/KEY: misc_difference
<222> LOCATION: (1)..(13)
<223> OTHER INFORMATION: phosphorothioate bond
<220> FEATURE:
<221> NAME/KEY: misc_difference
<222> LOCATION: (36)..(49)
<223> OTHER INFORMATION: phosphorothioate bond

<400> SEQUENCE: 33
tcgaacgttc gaatactcat tgatagacaa tgcgtttcga acgttcgaat            50

<210> SEQ ID NO 34
<211> LENGTH: 60
<212> TYPE: DNA
<213> ORGANISM: Artificial Sequence
<220> FEATURE:
<223> OTHER INFORMATION: anti-PD-L1 aptamer-CpG sequence
<220> FEATURE:
<221> NAME/KEY: misc_difference
<222> LOCATION: (1)..(14)
<223> OTHER INFORMATION: phosphorothioate bond
<220> FEATURE:
<221> NAME/KEY: misc_difference
<222> LOCATION: (46)..(59)
<223> OTHER INFORMATION: phosphorothioate bond

<400> SEQUENCE: 34
tcgaacgttc gaacgagtta tgctttcccc ctctttgata gacaattcga acgttcgaat    60
```